(12) United States Patent
Iles et al.

(10) Patent No.: US 6,481,267 B1
(45) Date of Patent: Nov. 19, 2002

(54) RHEOMETER

(75) Inventors: Christopher Martin Iles, Bourne End (GB); Ian David Bateson, Haslemere (GB); James Alfred Walker, Haslemere (GB)

(73) Assignee: Stable Micro Systems Limited (GB)

( * ) Notice: Subject to any disclaimer, the term of this patent is extended or adjusted under 35 U.S.C. 154(b) by 0 days.

(21) Appl. No.: 09/715,683

(22) Filed: Nov. 17, 2000

(30) Foreign Application Priority Data

Nov. 20, 1999 (GB) ............................................. 9927420

(51) Int. Cl.[7] .............................................. G01N 11/14
(52) U.S. Cl. ...................................................... 73/54.28
(58) Field of Search ............................ 73/54.28, 54.29, 73/54.31, 54.32, 54.33, 54.34, 54.38

(56) References Cited

U.S. PATENT DOCUMENTS

| | | | | |
|---|---|---|---|---|
| 2,171,312 A | * | 8/1939 | Meyers | 137/92 |
| 2,339,991 A | * | 1/1944 | Hagy | 137/92 |
| 2,491,639 A | * | 12/1949 | Bechtel et al. | 73/54.32 |
| 3,050,986 A | * | 8/1962 | Brazier | 137/92 |
| 3,455,145 A | * | 7/1969 | Gustafsson | 73/54.28 |

FOREIGN PATENT DOCUMENTS

| | | |
|---|---|---|
| EP | 798549 | 10/1997 |
| GB | 808740 | 2/1959 |
| GB | 1197850 | 7/1970 |
| GB | 2209370 | 5/1989 |
| GB | 2224083 | 4/1990 |
| JP | 56048234 | 1/1981 |
| WO | 9736162 | 10/1997 |

OTHER PUBLICATIONS

Search Report May 24, 2000.

* cited by examiner

*Primary Examiner*—Hezron Williams
*Assistant Examiner*—Michael Cygan
(74) *Attorney, Agent, or Firm*—Ira S. Dorman

(57) ABSTRACT

A rheometer incorporates a blade (1) mounted for rotation about an axis (2). The blade is of twisted form such that it has first and second regions. A first region of the blade (1) substantially at the axis of rotation (2) has a first angle formed by its surface with respect to a plane perpendicular to the axis of rotation such that the surface of the blade in the first region extends substantially parallel to the axis of rotation. A second region of the blade spaced from the axis of rotation has a second angle, different to the first angle, formed by its surface with respect to the plane perpendicular to the axis of rotation.

10 Claims, 4 Drawing Sheets

RHEOMETER

This invention relates to a rheometer incorporating a blade mounted for rotation about an axis.

BACKGROUND TO THE INVENTION

Rheometers are well known and used in a wide variety of chemical and material processing industries for assessing characteristics, such as flow characteristics, of materials such as powders, liquids and semi-solids such as pastes, gels, ointments and the like.

DESCRIPTION OF PRIOR ART

One particular rheometer is described in WO-A-9736162 in which blades extend substantially radially from a rotor shaft and are disposed at an angle relative to the axis of the shaft. The blades may be of twisted form; however the blade is at an angle over its entire length, relative to the axis of the shaft.

We have found that, although this arrangement of the prior art is generally satisfactory, some disadvantages can arise with regard to achieving repeatability when testing materials of different bulk density and rheology and particularly when comparing data derived from blades of different sizes.

OBJECT OF THE INVENTION

It is therefore an object of the present invention to provide a rheometer incorporating a blade which eliminates or at least ameliorates the above disadvantages.

SUMMARY OF THE INVENTION

According to the present invention there is provided a rheometer incorporating a blade mounted for rotation about an axis, wherein the blade is of twisted form such that:

a first region of the blade substantially at the axis of rotation has a first angle formed by its surface with respect to a plane perpendicular to the axis of rotation such that the surface of the blade in the first region extends substantially parallel to the axis of rotation; and a second region of the blade spaced from the axis of rotation has a second angle, different to the first angle, formed by its surface with respect to the plane perpendicular to the axis of rotation.

The blade may extend substantially at right angles to the axis of rotation, preferably substantially horizontally.

The second angle may vary with distance from the axis of rotation. For example, the second angle may decrease progressively with increasing distance from the axis of rotation.

The second angle may have a natural tangent which is inversely proportional to distance from the axis of rotation.

The rheometer may include means such that, in use, for each revolution of the blade, the blade is adapted to be displaceable by a predetermined lead distance along the axis of rotation, the second angle having a natural tangent defined as the predetermined lead distance divided by the distance of the point from the axis of rotation.

The height elevation of the twisted blade may be in mathematical proportion to blade lead distance, the blade lead distance being defined as the displacement of the blade along the axis of rotation for each revolution of the blade.

Alternatively, the height elevation of the twisted blade may be in mathematical proportion to blade diameter.

As a further alternative, the height elevation of the twisted blade may be in mathematical proportion to a ratio of blade lead distance, to blade diameter, the blade lead distance being defined as the displacement of the blade along the axis of rotation for each revolution of the blade.

The blade may be provided such that, prior to twisting, it has a progressively increasing width with increasing distance from the axis of rotation, whereby a substantially constant height elevation of the twisted blade is obtained.

The blade of the present invention demonstrates enhanced geometry compared with the prior art, enabling optimisation of performance and improved repeatability to be achieved in rheometers when used for testing materials of different bulk density and rheology. Data derived from blades of different sizes can be more reliably compared than hitherto.

For a better understanding of the present invention and to show more clearly how it may be carried into effect reference will now be made, by way of example, to the accompanying drawings in which:

DESCRIPTION OF PREFERRED EMBODIMENTS

Figure 1:
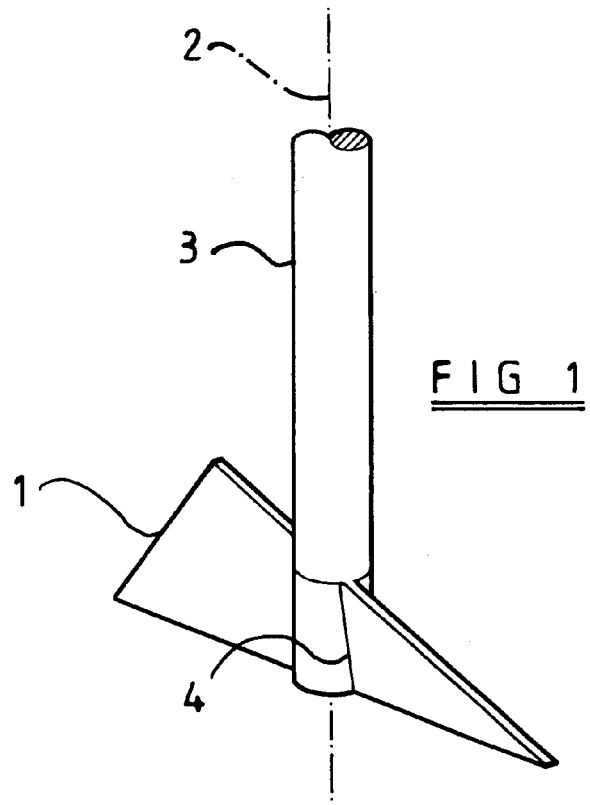
FIG. 1 is an isometric view of a blade for a rheometer according to the present invention.

Referring to FIG. 1, a blade 1 for a rheometer is arranged to be mountable in a rheometer for rotation about an axis 2 on a shaft 3. The blade 1 has a region 4 arranged substantially at the axis of rotation 2 and such that the surface of the blade at this region 4 is substantially parallel to the axis of rotation 2. This means that the blade 1 where connected to the shaft 3 has its major surface in that region aligned with the axis of rotation 2 and the shaft 3.

Figure 2:
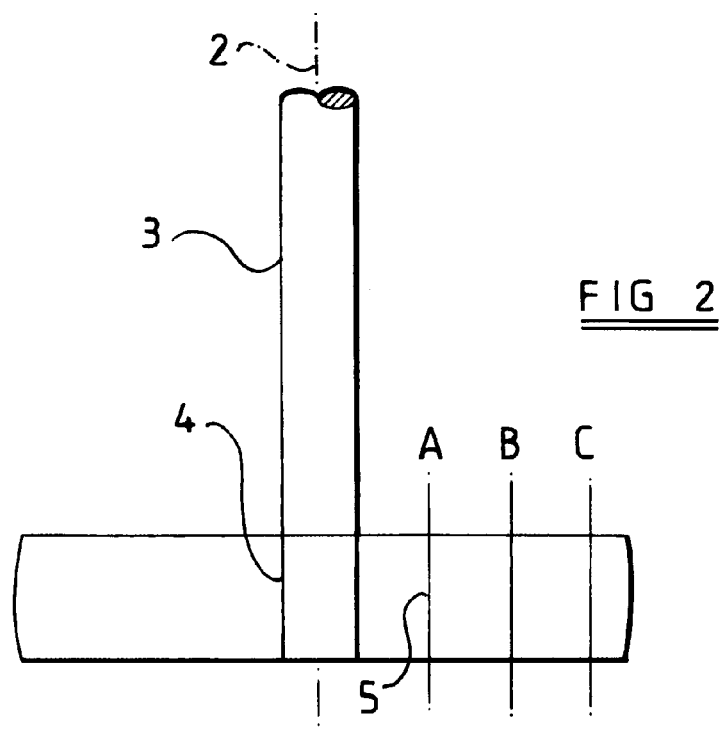
FIGS. 2 and 3 are side and end-on views of the blade of FIG. 1, illustrating the arrangement of the twisted blade.

The blade 1 extending outwards from that region is of twisted form and is arranged to extend radially, that is substantially at right angles to the axis of rotation 2 and preferably horizontally when in operation in a rheometer. As illustrated in FIG. 2, this means that at any one of locations A, B, C along the blade, straight line paths 5 drawn across the blade surface perpendicular to the blade edge will be parallel to the axis of rotation 2.

Figure 3:
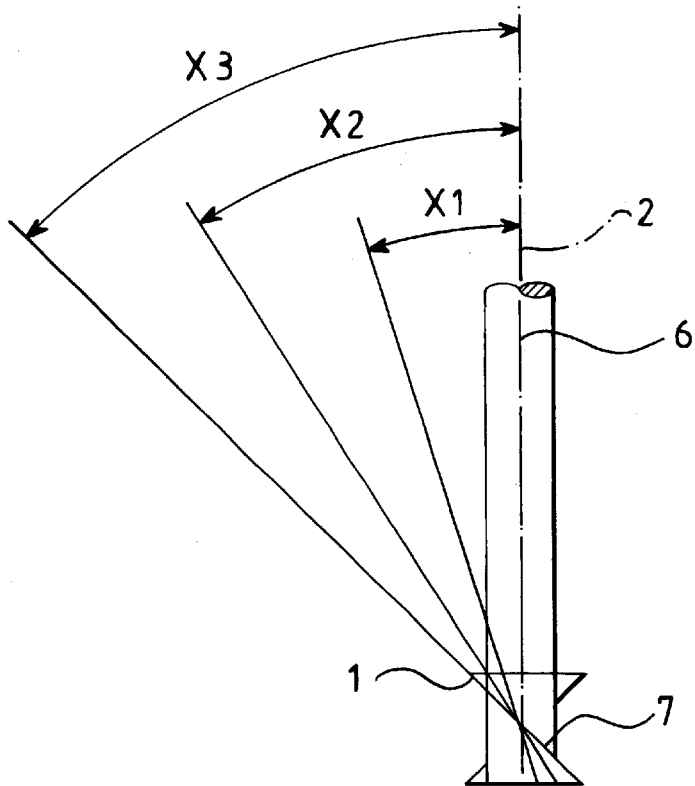

As illustrated in FIG. 3, reference numeral 6 refers to a plane through and along the blade 1, aligned with the axis of rotation 2. By way of explanation, such plane 6 through the axis of rotation extends effectively out of the plane of the paper. The twisted form of the blade results in the angle of surface 7 of the blade varying along the blade with respect to plane 6. Such angle X1, X2, X3, increases progressively with increasing distance along the blade from the axis of rotation 2. Correspondingly, the twisted form of the blade results in the angle of surface 7 of the blade decreasing progressively with regard to a plane perpendicular to the axis of rotation 2.

Figure 4:
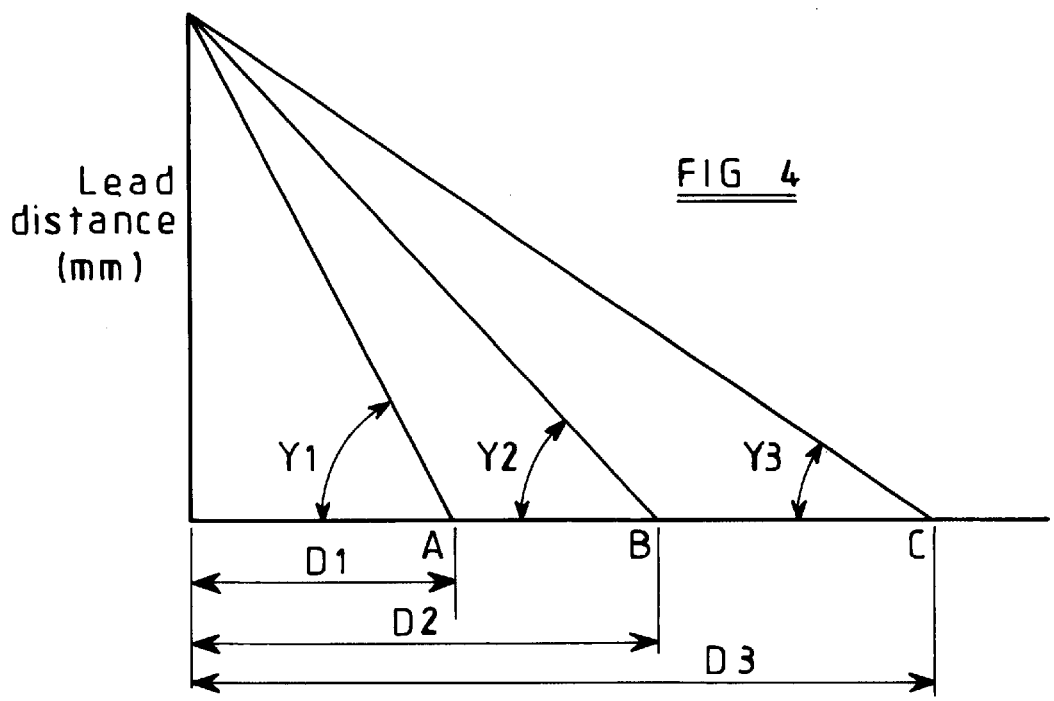
FIG. 4 is a diagram illustrating the angular twisting arrangement of the blade of FIG. 1 as a function of blade lead distance and distance from the axis of rotation.

When the blade 1 is in use in a rheometer, it is arranged that for each revolution of the blade, the blade is displaceable by a predetermined distance along the axis of rotation 2. Such predetermined distance will hereinafter be referred to as the lead distance. As shown in FIG. 4, the twisted blade 1 at any point A, B, C along its length has an angle Y1, Y2, Y3 formed by its surface with respect to ah plane perpendicular to the axis of rotation 2. Such angle Y1, Y2, Y3 has a natural tangent which is inversely proportional to the distance D1, D2, D3 of the respective point A, B, C from the axis of rotation, in particular a natural tangent which is defined as the lead distance divided by the distance D1, D2, D3. The defined angle Y1, Y2, Y3 decreases progressively with increasing distance D1, D2, D3 from the axis of rotation 2.

Figure 5A:
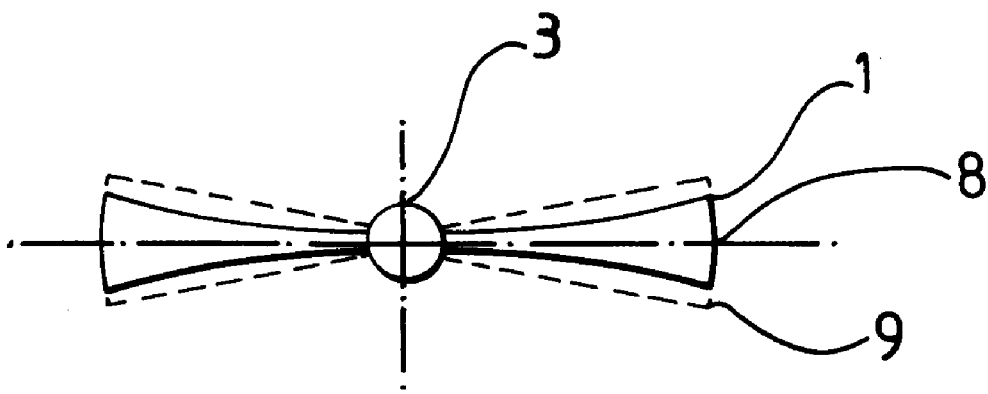
FIGS. 5A and 5B are diagrammatic representations of the effect of blade width geometry in the blade of FIG. 1.
Figure 5B:
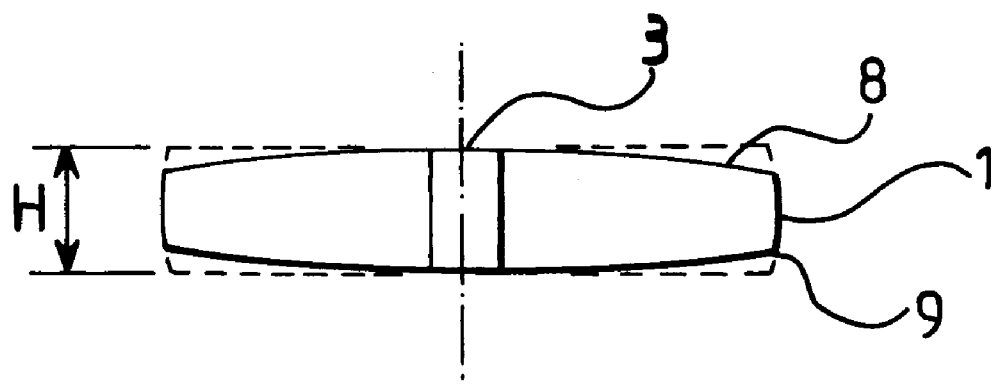

Although the blade 1 may be provided in its twisted form from an initially planar rectangular form, it is preferred that the initially planar form demonstrates progressively increasing width with increasing distance from what will be the axis of rotation in the finished twisted blade. The reason for this is illustrated in FIGS. 5A and 5B which show top and side views respectively of a blade 1 mounted on a shaft 3. If the blade 1 is formed from an initially planar rectangular form, the height elevation H of the resulting twisted blade is not constant along the length of the blade, but decreases along the length of the blade from the shaft 3, as denoted by reference numeral 8. If, however, the blade in its initially planar form is designed to have progressively increasing width with increasing distance from the shaft 3, the height elevation H of the resulting twisted blade can be made substantially constant along its length as denoted by reference numeral 9.

The height elevation H of the twisted blade can be arranged to be in mathematical proportion to the lead distance of the blade, or to the diameter of the blade, or to the ratio of these parameters, the lead distance, as previously defined, being the distance of displacement of the blade along its axis of rotation for each revolution of the blade.

The blade of the present invention demonstrates enhanced design geometry, enabling optimisation of performance and improved repeatability to be achieved in rheometers when used for testing materials of different bulk density and rheology. The specific design criteria according to the present invention can be applied to blades of different diameters so that data derived from different sized blades can be reliably compared.

A standard blade form can be adopted, with the overall blade diameter adjusted to suit the diameter of vessels containing a test material, such as a powder, into which the blade is to be inserted for operation.

When using test vessels and blade assemblies of different diameters, a constant ratio of lead distance to the distance from the axis of rotation to the end of the blade may be adopted whereby test results can be meaningfully related.

Figure 6:
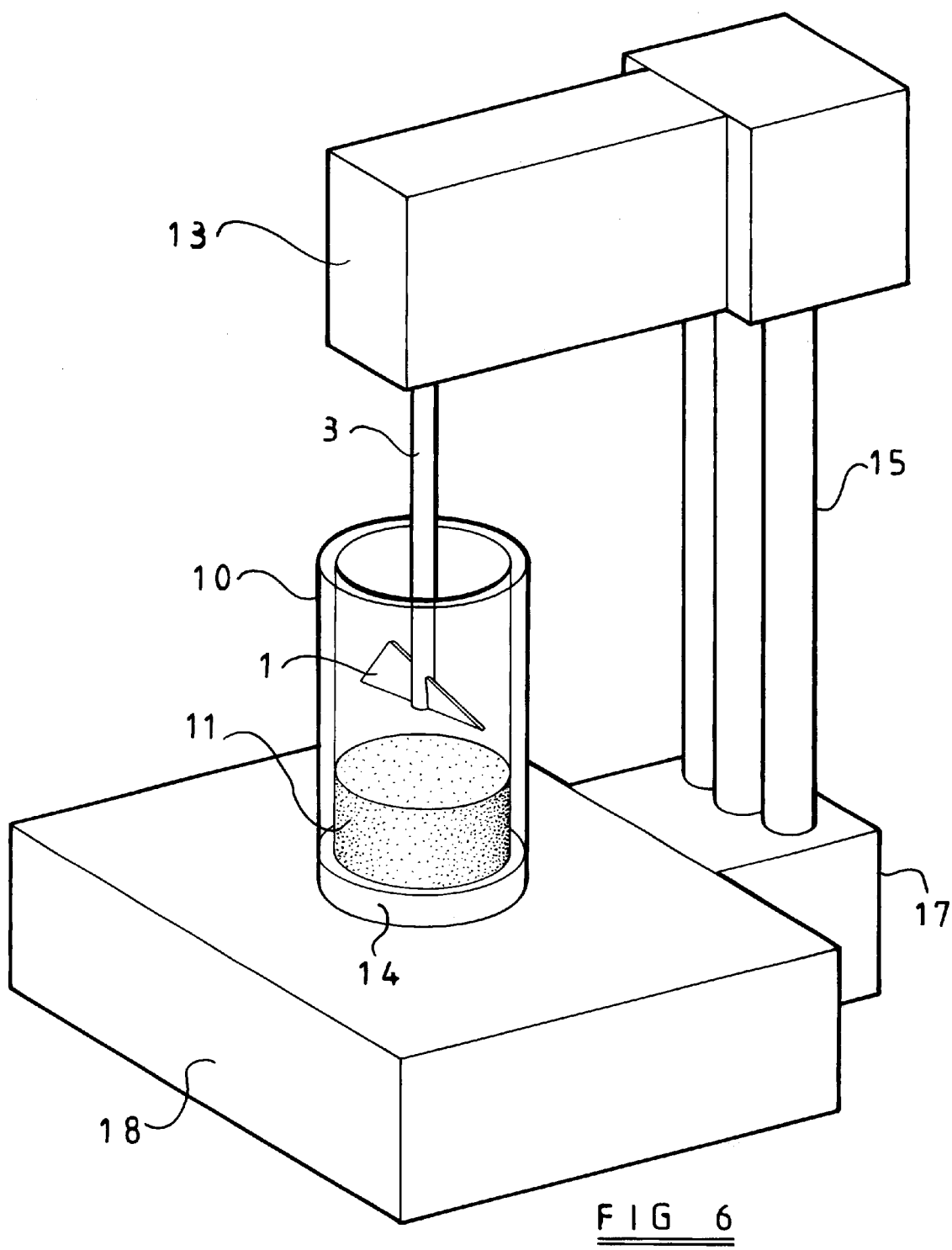
FIG. 6 is a diagrammatic illustration of an embodiment of a rheometer according to the present invention incorporating the blade of FIG. 1.

The blade 1 of the present invention, or a plurality of such blades, can be used in rheometers of well-known form. Such rheometers are described, for example, in WO-A9736162. FIG. 6 shows an embodiment of a rheometer in which the blade of the present invention is provided. The rheometer comprises a generally cylindrical vessel 10 for containing a material 11, such as a powder, to be assessed. A blade 1, as detailed in FIG. 1, is supported for rotation on a shaft 3 and is arranged as a close fit within the vessel 10. The blade is arranged to be rotated at a variable speed, either clockwise or anti-clockwise, by a variable speed device, such as a servo-motor, and gearbox unit 13.

The vessel 10 is supported on a torque and force measurement table 14. The blade can be raised or lowered in the axial direction of the vessel by means of a linear guidance system 15, operable at a variable velocity by means of a combined variable speed reversible drive and gearbox unit 17. The blade 1 is therefore able to undergo relative displacement along the axis of rotation of the shaft 3 with respect to the vessel 10 containing the material 11.

The combined movements of the blade and the vessel cause the blade to move along a helical path through the material 11 contained within the vessel 10.

A force and torque transducer unit 18 measures axial forces imposed on the material 11 as it is displaced and also measures torque imposed on the material.

The rheometer is controlled in known manner by a computer (not shown).

In an alternative arrangement, the blade 1 is fixed and the vessel 10 arranged to be raised or lowered around the blade.

We claim:

1. A blade rheometer incorporating a measuring blade mounted for rotation about an axis, wherein the blade is of twisted form such that:

a first region of the blade substantially at the axis of rotation has a first angle formed by its surface with respect to a plane perpendicular to the axis of rotation such that the surface of the blade in the first region extends substantially parallel to the axis of rotation; and a second region of the blade spaced from the axis of rotation has a second angle, different to the first angle, formed by its surface with respect to the plane perpendicular to the axis of rotation, the second angle varying with distance from the axis of rotation; and including means such that, in use, for each revolution of the blade, the blade is adapted to be displaceable by the predetermined lead distance along the axis of rotation, the second angle having a natural tangent defined as the predetermined lead distance divided by the distance of the point from the axis of rotation.

2. A rheometer as claimed in claim 1, wherein the blade extends substantially at right angles to the axis of rotation.

3. A rheometer as claimed in claim 2, wherein the blade extends substantially horizontally.

4. A rheometer as claimed in claim 1, wherein the height elevation of the twisted blade is in mathematical proportion to blade lead distance, the blade lead distance being defined as the displacement of the blade along the axis of rotation for each revolution of the blade.

5. A rheometer as claimed in claim 1, wherein the height elevation of the twisted blade is in mathematical proportion to blade diameter.

6. A rheometer as claimed in claim 1, wherein the height elevation of the twisted blade is in mathematical proportion to a ratio of blade lead distance, to blade diameter, the blade lead distance being defined as the displacement of the blade along the axis of rotation for each revolution of the blade.

7. A rehometer as claimed in claim 1, wherein the blade is provided such that, prior to twisting, it has a progressively increasing width with increasing distance from the axis of rotation, whereby a substantially constant height elevation of the twisted blade is obtained.

8. A blade rheometer incorporating a measuring blade mounted for rotation about an axis, wherein the blade is of twisted form such that:

a first region of the blade substantially at the axis of rotation has a first angle formed by its surface with respect to a plane perpendicular to the axis of rotation such that the surface of the blade in the first region extends substantially parallel to the axis of rotation; and a second region of the blade spaced from the axis of rotation has a second angle, different to the first angle, formed by its surface with respect to the plane perpendicular to the axis of rotation, the second angle varying with distance from the axis of rotation; and wherein the blade is provided such that, prior to twisting, it has a progressively increasing width with increasing distance from the axis of rotation, whereby a substantially constant height elevation of the twisted blade is obtained.

9. A rheometer as claimed in claim 8, wherein the blade extends substantially at right angles to the axis of rotation.

10. A rheometer as claimed in claim 9, wherein the blade extends substantially horizontally.

* * * * *